(12) United States Patent
Wershofen et al.

(10) Patent No.: US 7,662,989 B2
(45) Date of Patent: Feb. 16, 2010

(54) PROCESS FOR THE PREPARATION OF LIQUID, STORAGE-STABLE ORGANIC ISOCYANATES CONTAINING CARBODIIMIDE AND/OR URETONIMINE GROUPS

(75) Inventors: Stefan Wershofen, Monchengladbach (DE); Marcus Steinwegs, Krefeld (DE)

(73) Assignee: Bayer Materialscience AG, Leverkusen (DE)

( * ) Notice: Subject to any disclaimer, the term of this patent is extended or adjusted under 35 U.S.C. 154(b) by 226 days.

(21) Appl. No.: 11/649,000

(22) Filed: Jan. 3, 2007

(65) Prior Publication Data

US 2007/0155938 A1 Jul. 5, 2007

(30) Foreign Application Priority Data

Jan. 5, 2006 (DE) .................. 10 2006 000 825

(51) Int. Cl.
*C07C 251/00* (2006.01)
*C07C 291/00* (2006.01)

(52) U.S. Cl. .................. 560/334; 540/200; 548/951; 548/952

(58) Field of Classification Search .............. 560/334, 560/25, 26, 115, 158; 252/182.2, 182.21, 252/182.22; 548/951, 952; 540/200
See application file for complete search history.

(56) References Cited

U.S. PATENT DOCUMENTS

| | | | | |
|---|---|---|---|---|
| 2,853,473 A | | 9/1958 | Campbell et al. .......... 260/77.5 |
| 4,067,820 A | * | 1/1978 | Wagner et al. ............. 502/159 |
| 4,088,665 A | | 5/1978 | Findeisen et al. .... 260/453 AM |
| 4,120,884 A | * | 10/1978 | Woerner et al. ............ 560/331 |
| 4,284,730 A | | 8/1981 | Narayan et al. ............ 521/160 |
| 5,202,358 A | | 4/1993 | Scholl et al. ................ 521/160 |
| 5,354,888 A | | 10/1994 | Scholl ........................ 564/252 |
| 5,610,408 A | * | 3/1997 | Imokawa et al. ......... 252/182.2 |
| 6,120,699 A | | 9/2000 | Narayan et al. .......... 252/182.2 |
| 2006/0025557 A1 | | 2/2006 | Wershofen et al. ............ 528/44 |
| 2006/0128928 A1 | | 6/2006 | Wershofen et al. |
| 2007/0155937 A1 | | 7/2007 | Wershofen et al. |
| 2007/0155939 A1 | | 7/2007 | Wershofen et al. |
| 2007/0167633 A1 | | 7/2007 | Wershofen et al. |

FOREIGN PATENT DOCUMENTS

GB 1 356 851 6/1974

* cited by examiner

*Primary Examiner*—Randy Gulakowski
*Assistant Examiner*—Michael Leonard
(74) *Attorney, Agent, or Firm*—N. Denise Brown; Noland J. Cheung

(57) ABSTRACT

The invention relates to a process for the preparation of liquid, storage-stable isocyanate mixtures of low color number containing carbodiimide (CD) and/or uretonimine (UI) groups, the isocyanate mixtures obtainable by this process, the preparation of blends with further isocyanates and the process of the preparation of prepolymers containing isocyanate groups and/or polyurethane plastics, preferably polyurethane foams, from these isocyanate mixtures.

17 Claims, No Drawings

US 7,662,989 B2

PROCESS FOR THE PREPARATION OF LIQUID, STORAGE-STABLE ORGANIC ISOCYANATES CONTAINING CARBODIIMIDE AND/OR URETONIMINE GROUPS

CROSS REFERENCE TO RELATED PATENT APPLICATION

The present patent application claims the right of priority under 35 U.S.C. §119 (a)-(d) of German Patent Application No. 10 2006 000 825, filed Jan. 5, 2006.

BACKGROUND OF THE INVENTION

The invention relates to a process for the preparation of liquid, storage-stable isocyanate mixtures of low color number containing carbodiimide (CD) and/or uretonimine (UI) groups, the isocyanate mixtures obtainable by this process, the preparation of blends from these isocyanate mixtures with additional isocyanates, and to a process for the preparation of prepolymers containing isocyanate groups and of polyurethane plastics, and preferably polyurethane foams.

Isocyanate mixtures containing CD and/or UI groups can be prepared in a simple manner using the highly active catalysts from the phospholine series, and particularly the phospholine oxide series of catalysts. Such isocyanate mixtures are prepared by the processes as described in U.S. Pat. Nos. 2,853,473, 6,120,699 and EP-A-515 933.

The high catalytic activity of the phospholine catalysts, and specifically of the phospholine oxide catalysts, on the one hand is desirable in order to start up the carbodiimidization reaction under gentle temperature conditions. However, on the other hand, no process is known to date which ensures effective termination of the phospholine catalysis or phospholine oxide catalysis without limitation. The carbodiimidized isocyanates tend to after-react, i.e. they release gas as a result of evolution of $CO_2$. This then leads to a build up of pressure, for example, in the storage tanks, and especially at higher temperatures.

There has been no lack of attempts to discover an effective means of terminating the phospholine catalysis. Various terminators are mentioned, for example, in the patent specifications DE-A-25 37 685, EP-A-515 933, EP-A-609 698 and U.S. Pat. No. 6,120,699. These terminators include, for example, acids, acid chlorides, chloroformates, silylated acids and halides of the main group elements. The termination of the phospholine catalysts with acids, which, for example, can also be in the form of acid chlorides, is not sufficiently effective.

According to the teaching of EP-A-515 933, CD/UI-containing isocyanate mixtures prepared by means of phospholine catalysis are terminated with at least an equimolar amount, and preferably from 1 to 2 times the molar amount, based on the catalyst employed, of e.g. trimethylsilyl trifluoromethanesulfonate (TMST). In practice, however, it has been found that CD/UI-containing isocyanates prepared in such a way are of only limited suitability for the preparation of prepolymers, i.e. reaction products of these CD/UI-containing isocyanates with polyols. The correspondingly prepared reaction products of polyols and the CD/UI-modified isocyanates tend to release gas, which can lead to a build up of pressure in the transportation tanks or to foaming during the handling of such products.

This problem can be by-passed by employing the silylated acid to terminate the phospholine catalyst analogously to EP-A-515 933 in higher molar equivalents (e.g. 5:1-10:1, based on the catalyst). In practice, however, it is then found that the resultant CD/UI-modified isocyanates have a significantly poorer color number. This then also applies to the prepolymers prepared therefrom.

This also applies if the phospholine catalyst is terminated with acids of the trifluoromethanesulfonic acid type, in accordance with U.S. Pat. No. 6,120,699. Prepolymers prepared from these CD/UI-modified isocyanates also have a considerably increased color number.

In the preparation of liquid, storage-stable isocyanate mixtures containing carbodiimide (CD) and/or uretonimine (UI) groups, significant variations are sometimes observed in the reactivity of the isocyanate employed, and therefore, in the reaction times required. An undesirable prolonging of the reaction time could be counteracted, for example, by increasing the reaction temperature and/or the catalyst concentration (and as a result the amount of terminator). However, this would be associated with process and/or safety risks and/or quality problems (such as, for example, increased color values).

Thus, the object of the present invention was to provide a simple and economical process for the preparation of liquid, storage-stable and light-colored isocyanate mixtures which contain carbodiimide and/or uretonimine groups that do not have the deficiencies referred to, and leads to liquid, storage-stable isocyanate mixtures of low color numbers.

SUMMARY OF THE INVENTION

The invention relates to a process for the preparation of organic isocyanates containing carbodiimide and/or uretonimine groups. This process comprises partially carbodiimidizing one or more organic isocyanates having a Hazen color number of $\leq 100$ APHA, preferably $\leq 50$ APHA, with one or more catalysts of the phospholine type, and one or more ortho-esters; and subsequently terminating the carbodiimidization reaction. By means of this process, the required reaction time can be lowered or kept low and/or the amount of catalyst required can be reduced.

In accordance with the process of the invention, one ortho-ester or also a mixture of several different ortho-esters can be employed. In this context, the ortho-ester can be added directly to the starting isocyanate or to the reaction mixture during the carbodiimidization. The ortho-ester is preferably added here in substance, i.e. without dilution, or as a masterbatch. A suitable masterbatch is, for example, present as a solution of the ortho-ester in the starting isocyanate or in the already carbodiimidized isocyanate.

The present invention also relates to the organic isocyanates containing carbodiimide and/or uretonimine groups which are obtainable by the abovementioned process. These organic isocyanates containing carbodiimide and/or uretonimine groups are liquid at room temperature, and, depending on the CD/UI content and/or on the isocyanate employed, may be liquid down to low temperatures (e.g. 0° C.).

The present invention also provides a process for the preparation of isocyanate blends. These blends comprise the organic isocyanates containing carbodiimide and/or uretonimine groups according to the invention, and at least one other isocyanate component which is different than the isocyanates of the invention which contain carbodiimide and/or uretonimine groups. This invention also provides a process for the preparation of prepolymers which contain isocyanate groups and exhibit an improved color number from the isocyanates containing CD and/or UI groups of this invention.

Finally, the invention also provides a process for the preparation of polyurethane plastics, and preferably polyurethane foams, comprising reacting the organic isocyanates containing carbodiimide and/or uretonimine groups of the invention with at least one isocyanate-reactive component.

DETAILED DESCRIPTION OF THE INVENTION

As described and used herein, the Hazen color number can be measured in accordance with DIN/EN/ISO 6271-2 (draft of September 2002) in substance against water as the reference, at a layer thickness of 5 cm. For the measuring instrument, a Dr. Lange LICO 300 photometer e.g. can be employed.

Organic isocyanates having a higher color number can, of course, also be used as starting substances. When these higher color number isocyanates are used, however, the advantages with respect of the favorable color values are not utilized to the full extent.

Suitable organic isocyanates to be used as starting materials for the present invention include any desired organic isocyanates which have a Hazen color number of $\leq 100$ APHA, preferably $\leq 50$ APHA. It is preferred that the process according to the invention provides for the carbodiimidization of organic diisocyanates which can in turn be employed in polyurethane chemistry.

Organic isocyanates having a higher color number can, of course, also be used as starting substances. In this case, however, the advantages with respect to the favorable color values cannot be utilized to the full extent.

Suitable isocyanates to be used in accordance with the present invention include, for example, aromatic, araliphatic, aliphatic and/or cycloaliphatic diisocyanates and/or polyisocyanates.

Representatives of the aliphatic and/or cycloaliphatic diisocyanates which may be mentioned by way of example are isophorone-diisocyanate, hexamethylene-diisocyanate and dicyclohexylmethane-diisocyanate. In each case, the pure isomers and/or any desired isomer mixtures may be used herein.

Representatives of the araliphatic diisocyanates which may be mentioned by way of example are the various isomers of xylidene-diisocyanates.

Aromatic di- and polyisocyanates, such as toluene-diisocyanate, and di- and polyisocyanates of the diphenylmethane series, are suitable for the starting isocyanate component of the present invention.

In particular, the following isocyanates are suitable starting materials:

aromatic diisocyanates, such as 2,4- and/or 2,6-diisocyanatotoluene (TDI), 2,2'-, 2,4'- and/or 4,4'-diisocyanatodiphenylmethane (MDI) and any desired mixtures of such aromatic diisocyanates;
and di- and polyisocyanate mixtures of the diphenylmethane series having a content of monomeric diisocyanatodiphenylmethane isomers of from 80 to 100 wt. % and a content of polyisocyanates of the diphenylmethane series which are more than difunctional of from 0 to 20 wt. %, with the diisocyanatodiphenylmethane isomers being composed of 0 to 100% by weight of 4,4'-diisocyanatodiphenylmethane, 100 to 0% by weight of 2,4'-diisocyanatodiphenylmethane, and 0 to 8% by weight of 2,2'-diisocyanatodiphenylmethane, with the sum of the percentages of the three isomers totalling 100% by weight of the monomer.

Organic isocyanates which are preferred as starting materials are, in particular, aromatic diisocyanates, such as 2,4- and/or 2,6-diisocyanatotoluene (TDI), 2,2'-, 2,4'- and/or 4,4'-diisocyanatodiphenylmethane (MDI) and any desired mixtures of such aromatic diisocyanates. More preferred starting materials are 2,2'-, 2,4'- and/or 4,4'-diisocyanatodiphenylmethane (MDI) and any desired mixtures of such aromatic diisocyanates, with the sum of 2,2'-, 2,4'- and/or 4,4'-diisocyanato-diphenylmethane in the starting material (organic isocyanate) being at least 85% by weight of the total weight, and the diisocyanatodiphenylmethane isomers being composed of from 0 to 100% by weight of 4,4'-diisocyanatodiphenylmethane, from 100 to 0% by weight of 2,4'-diisocyanatodiphenylmethane and of from 0 to 8% by weight of 2,2'-diisocyanatodiphenylmethane, with the sum of the percentages stated totalling 100% by weight. Most preferred starting materials are 2,2'-, 2,4'- and/or 4,4'-diisocyanatodiphenylmethane (MDI), and any desired mixtures of aromatic diisocyanates, with the sum of 2,2'-, 2,4'- and/or 4,4'-diisocyanatodiphenylmethane in the starting material (i.e. the starting organic isocyanate) being at least 90% by weight, and the diisocyanatodiphenylmethane isomers being composed of 0 to 100% by weight of 4,4'-diisocyanato-diphenylmethane, 100 to 0% by weight of 2,4'-diisocyanatodiphenylmethane and 0 to 8% by weight of 2,2'-diisocyanatodiphenylmethane, with the sum of the percentages of the three isomers totalling 100% by weight. Most particularly preferred starting materials are 2,2'-, 2,4'- and/or 4,4'-diisocyanatodiphenylmethane (MDI) and any desired mixtures of aromatic diisocyanates, with the sum of 2,2'-, 2,4'- and/or 4,4'-diisocyanatodiphenylmethane present in the starting material (i.e. the starting organic isocyanate) being at least 99% by weight and the diisocyanatodiphenylmethane isomers being composed of 0 to 100% by weight of 4,4'-diisocyanatodiphenylmethane, 100 to 0% by weight of 2,4'-diisocyanatodiphenylmethane, and 0 to 8% by weight of 2,2'-diisocyanatodiphenylmethane, with the sum of the percentages stated for the three isomers totalling 100% by weight.

The process according to the invention is carried out in the presence of catalysts of the phospholine type. The catalysts of the phospholine type are known and described in, for example, EP-A-515 933 and U.S. Pat. No. 6,120,699, the disclosures of which are hereby incorporated by reference. Typical examples of these catalysts are, for example, the mixtures, known from the prior art, of the phospholine oxides which correspond to the formulas:

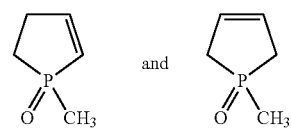

The amount of catalyst employed depends on the quality and/or the reactivity of the starting isocyanates. Thus, the specific amount of catalyst needed can most easily and readily be determined in a preliminary experiment.

By using ortho-esters, the reactivity of the starting isocyanate is increased. This can occur, for example, because these ortho-esters counteract the reactivity-reducing action of secondary components in the starting isocyanate which potentially split off HCl (i.e. hydrochloric acid). Other action mechanisms are, however, also possible.

Suitable ortho-esters to be used in accordance with the present invention include, for example, ortho-esters of carboxylic acids. Suitable ortho-esters of carboxylic acids will typically correspond to the general structure:

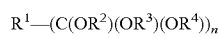

wherein
R¹ represents an aliphatic, cycloaliphatic, aromatic or araliphatic hydrocarbon radical which can contain heteroatoms and which can optionally contain further functional groups;

R² to R⁴ each independently represents an aliphatic, cycloaliphatic, aromatic or araliphatic hydrocarbon radical which can optionally contain heteroatoms and which can optionally contain additional functional groups;

and n represent a number ≧1.

In the general structure set forth above for ortho-esters of carboxylic acids, R², R³ and R⁴ can be either all identical or all different, or two of the three radicals R², R³ and R⁴ can be identical and the third different. Likewise, it is possible for two or three of the radicals R², R³ and R⁴ to be parts of a single molecule and thus, for cyclic or bicyclic ortho-ester structures to be present.

Some examples of suitable ortho-esters of carboxylic acids include, for example, ortho-esters of formic acid, such as e.g. trimethyl orthoformate, triethyl orthoformate, ortho-esters of acetic acid, such as e.g. trimethyl orthoacetate, triethyl orthoacetate, ortho-esters of propionic acid, such as e.g. trimethyl orthopropionate, triethyl orthopropionate, or mixtures thereof.

The compounds mentioned herein are regarded only as examples; suitable ortho-esters of carboxylic acids are not limited in scope to the compounds mentioned herein.

Suitable ortho-esters to be used in the present invention also include, for example, the ortho-esters of carbonic acid. Suitable ortho-esters of carbonic acid will typically correspond to the general structure:

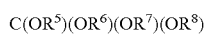

$C(OR^5)(OR^6)(OR^7)(OR^8)$ wherein:
R⁵ to R⁸ each independently represents an aliphatic, cycloaliphatic, aromatic or araliphatic hydrocarbon radical which can optionally contain heteroatoms and which can optionally contain additional functional groups.

In the general structure above for the ortho-esters of carbonic acid, R⁵, R⁶, R⁷ and R⁸ can be either all identical or all different, or two of the radicals R⁵, R⁶, R⁷ and R⁸ can in each case be identical, or two or three of the radicals R⁵, R⁶, R⁷ and R⁸ can be identical. Likewise, it is possible for two or in each case two or three of the radicals R⁵, R⁶, R⁷ and R⁸ to be parts of a single molecule and thus, for cyclic or bicyclic ortho-ester structures to be present.

Some examples of suitable ortho-esters of carbonic acid include compounds such as, for example, tetramethyl orthocarbonate and tetraethyl orthocarbonate or mixtures thereof. The compounds mentioned are regarded only as examples of suitable compounds. Suitable ortho-esters of carbonic acid for the present invention are not limited to the compounds expressly mentioned herein.

Suitable ortho-esters to be used in accordance with the present invention include, for example the ortho-esters of silicic acid. Suitable ortho-esters of silicic acid will typically correspond to the general structure:

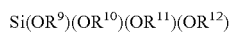

$Si(OR^9)(OR^{10})(OR^{11})(OR^{12})$ wherein:
R⁹ to R¹² each independently represents an aliphatic, cycloaliphatic, aromatic or araliphatic hydrocarbon radical which can optionally contain heteroatoms and which can optionally contain additional functional groups.

In the above general structure, R⁹ to R¹² can be either all identical or all different, or two of the radicals R⁹, R¹⁰, R¹¹ and R¹² can in each case be identical, or two or three of the radicals R⁹, R¹⁰, R¹¹ and R¹² can be identical. It is likewise possible for two or in each case two or three of the radicals R⁹, R¹⁰, R¹¹ and R¹² to be parts of a single molecule and thus, for cyclic or bicyclic ortho-ester structures to be present.

Some examples of suitable ortho-esters of silicic acid compounds include, for example, tetramethyl orthosilicate and tetraethyl orthosilicate or mixtures thereof. The compounds mentioned are regarded only as examples. Suitable ortho-esters of silicic acid for the present invention are not limited to the compounds expressly mentioned herein.

In accordance with the present invention, the ortho-ester or the mixture of several different ortho-esters can be added immediately before, at the same time as, or also, only after the addition of the catalyst to the starting isocyanate. Preferably, the ortho-ester is added only after the addition of the catalyst, i.e. during the carbodiimidization reaction. The best point in time of the addition of the ortho-ester can be determined in a simple preliminary experiment, and is preferably before reaching 50%, more preferably before reaching 30% and most preferably before reaching 20% of the total desired conversion of isocyanate.

The optimum amount of the ortho-ester which is employed can likewise be determined in a simple preliminary experiment. It is preferred to use ≦1,000 ppm, more preferred to use ≦250 ppm and most preferred to use ≦100 ppm, based on the weight of the starting isocyanate employed.

The ortho-ester can thus be added directly to the starting isocyanate, or to the reaction mixture during the carbodiimidization reaction. In this context, the ortho-ester is preferably added in substance, i.e. without dilution, or as a masterbatch. A masterbatch, for example, provides a solution of the ortho-ester in the starting isocyanate or in already carbodiimidized isocyanate.

The addition of the ortho-ester results in a higher reactivity with respect to the carbodiimidization reaction. As a result of this higher reactivity, either the reaction time required and/or the amount of catalyst required can be reduced.

The carbodiimidization reaction is conventionally carried out in the temperature range between 50 to 150° C., preferably from 60 to 100° C. However, significantly higher reaction temperatures are also possible (i.e. up to approx. 280° C.). The optimum reaction temperature for the carbodiimidization reaction depends on the nature of the starting isocyanates and/or of the catalyst employed, and can be determined in a simple preliminary experiment.

The carbodiimidization reaction is, in general, interrupted when a degree of carbodiimidization of from 3 to 50%, and preferably from 5 to 30%, is reached. The phrase "the degree of carbodiimidization" refers to the percentage of carbodiimidized isocyanate groups, with respect to the total amount of isocyanate groups present in the starting isocyanate.

The degree of carbodiimidization can be determined while the process according to the invention is being carried out, by determination of the % NCO by, for example, means of titration, which is known per se to the person skilled in the art, or by means of suitable online methods. A suitable online method is, for example, near infra-red or middle infra-red analysis.

The degree of carbodiimidization can likewise be ascertained while the process according to the invention is being carried out, for example, from the amount (i.e. quantity) of carbon dioxide escaping in the reactor mixture. This amount of carbon dioxide, which can be determined volumetrically, thus provides information about the degree of carbodiimidization reached at any point in time.

Furthermore, in principle, other suitable offline or online methods of process monitoring which are known to the person skilled in the art can also be employed.

To end the carbodiimidization reaction, it is preferable to add at least the equimolar amount, more preferably a 1- to 20-fold molar excess, and most preferably a 1- to 10-fold molar excess, based on the weight of the catalyst, of a terminator or an alkylating agent. A mixture of terminators may also be employed. A preferred catalyst terminator is trimethylsilyl trifluoromethanesulfonate (TMST). In this context, an alkylating agent or trimethylsilyl trifluoromethanesulfonate (TMST) is preferably employed as the sole terminator.

Preferred alkylating agents are esters of trifluoromethanesulfonic acid, esters of inorganic acids (preferably strong inorganic acids) or trialkyloxonium compounds.

The reaction product of the carbodiimidization reaction can contain color stabilizers such as those which are conventionally added to isocyanates. In this context, the point in time of the addition of the stabilizers is not critical. The color stabilizers can be added either to the isocyanate which is used as the starting material, before the carbodiimidization, or to the reaction product when the carbodiimization reaction has ended. Likewise, it is possible to add color stabilizers to both the starting material and to the reaction product. Such stabilizers are generally known to the person skilled in the art and include e.g. substances from the group consisting of sterically hindered phenols, phosphorous acid esters or sterically hindered amines. The color stabilizers can in each case be employed by themselves or in a mixture with other representatives of the same or different substance groups. The amounts of color stabilizers employed varies in the order of magnitude known to the person skilled in the art, conventionally in the range of from 100 ppm to 10,000 ppm for the individual substance or the mixture, based on the total weight of the isocyanate used as the starting material or of the reaction product of the carbodiimidization.

Prepolymers containing isocyanate groups are obtained by, for example, reaction of the organic isocyanates containing carbodiimide and/or uretonimine groups which are prepared by the process of the present invention with one or more conventional polyols which are known to be suitable in polyurethane chemistry. Suitable polyols include both simple polybasic alcohols having a molecular weight in the range of from 62 to 599 g/mol, preferably 62 to 300 g/mol, such as e.g. ethylene glycol, trimethylolpropane, propane-1,2-diol, butane-1,2-diol or butane-2,3-diol, hexanediol, octanediol, dodecanediol and/or octadecanediol, and in particular, higher molecular weight polyether polyols and/or polyester polyols of the type known per se from polyurethane chemistry which have molecular weights of from 600 to 8,000 g/mol, preferably 800 to 4,000 g/mol. Such higher molecular weight compounds typically contain at least two, and as a rule from 2 to 8, and preferably from 2 to 4 primary and/or secondary hydroxyl groups. Examples of such polyols are described in, for example, U.S. Pat. No. 4,218,543, at column 7, line 29 to column 9, line 32, the disclosure of which is hereby incorporated by reference.

The advantages of the process according to the invention are apparent: The reactivity of the reaction mixture is increased and/or standardized by the presence of an ortho-ester during the carbodiimidization. As a result, the required reaction time can be lowered or kept low and/or the required amount of catalyst can be reduced. Both the isocyanates containing carbodiimide and/or uretonimine groups and the prepolymers prepared therefrom furthermore have a good storage stability and a light color.

These organic isocyanates containing carbodiimide and/or uretonimine groups and the prepolymers prepared therefrom by reaction of the isocyanates of the invention with polyols are valuable starting materials for the preparation of polyurethane plastics by the reaction of the isocyanates of the invention or prepolymers thereof with one or more polyols (e.g. polyether polyols and/or polyester polyols) by the isocyanate polyaddition process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The following starting substances were used in the working examples:

Isocyanate A: 4,4'-diphenylmethane diisocyanate having an NCO group content of 33.6% by weight (Desmodur 44M®, Bayer AG)

Catalyst A: a technical-grade mixture of 1-methyl-1-oxo-1-phosphacyclopent-2-ene and 1-methyl-1-oxo-1-phosphacyclopent-3-ene, 1 wt. % strength in toluene Terminator A: trimethylsilyl trifluoromethanesulfonate (TMST)

Ortho-Ester A: triethyl orthoacetate

The following general instructions were used for the preparation of the organic isocyanate containing carbodiimide and/or uretonimine groups:

10 kg of Isocyanate A having a Hazen color number of <15 APHA, which contained 750 ppm 3,5-di-tert-butyl-4-hydroxytoluene, were heated to approx. 90° C. under $N_2$ while stirring. The amount of catalyst solution as shown in the table in order to achieve the desired amount of catalyst was then added. The corresponding amount of the ortho-ester was added to the reaction mixture (see the table for details including the specific point in time of the addition of the ortho-ester, and the amount of ortho-ester added in each example). The reaction mixture was heated at approx. 95° C. under $N_2$/while stirring until the desired NCO content was reached. Thereafter, the carbodiimidization reaction was terminated by the addition of the terminator (i.e. trimethylsilyl trifluoromethanesulfonate (TMST)) and the mixture was subsequently stirred for 1 hour.

The results are summarized in the following table.

The Hazen color number was measured in accordance with DIN/EN/ISO 6271-2 (draft of September 2002), in substance against water as the reference at a layer thickness of 5 cm. A Dr. Lange LICO 300 photometer was employed as the measuring instrument.

| | Educt | | | | | Reaction conditions | | | |
|---|---|---|---|---|---|---|---|---|---|
| | Hydrolysable chlorine [ppm] | Catalyst concentration [ppm] | Terminator | Terminator concentration [ppm] | Ortho-ester | Conc. of the ortho-ester [ppm] | Time of addition of the ortho-ester after addition of catalyst | Reaction time [min] | Product NCO value [%] |
| Comparison Example 1 | 10 | 2.5 | TMST | 50 | — | — | — | 310 | 29.4 |
| Comparison Example 2 | 20 | 2.5 | TMST | 50 | — | — | — | 360 | 31.6 |
| Example 1 | 19 | 2.5 | TMST | 50 | A | 100 | 120 | 395 | 29.5 |

Comparison Examples 1 and 2 illustrate the adverse influence of the increased value of hydrolysable chlorine on the reactivity or the reaction time. In the example according to the invention (i.e. Example 1), an improved reactivity is achieved compared with Comparison Example 2 for the same content of hydrolysable chlorine; after 360 min the NCO value in Comparison Example 2 had fallen from originally approx. 33.6% only to 31.6%, compared with 29.5% in Example 1 which is representative of the invention.

The comparison of Comparison Example 1 and Example 1 shows that the addition of the ortho-ester, at twice the content of hydrolysable chlorine, a comparable reactivity is again achieved, i.e. a comparable reaction time for achieving the same NCO value is rendered possible.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of organic isocyanates containing carbodiimide and/or uretonimine groups, comprising
   (A) partially carbodiimidizing
      (1) one or more organic isocyanates having a Hazen color number of $\leq 100$ APHA,
      in the presence of
      (2) one or more phospholine catalysts,
      and
      (3) one or more ortho-esters selected from the group consisting of ortho-esters of a carboxylic acid, ortho-esters of a carbonic acid and ortho-esters of a silicic acid;
      and, subsequently,
   (B) terminating the carbodiimidization reaction.

2. The process of claim 1, wherein said one or more organic isocyanates has a Hazen color number of $\leq 50$ APHA.

3. The process of claim 1, wherein (3) said ortho-ester of a carboxylic acid corresponds to the general structure:

$$R^1-(C(OR^2)(OR^3)(OR^4))_n,$$

wherein:
   $R^1$: represents an aliphatic, cycloaliphatic, aromatic or araliphatic hydrocarbon radical which can optionally contain heteroatoms and which can optionally carry further functional groups,
   $R^2$ to $R^4$: each independently represent an aliphatic, cycloaliphatic, aromatic or araliphatic hydrocarbon radical which can optionally contain heteroatoms, and which can optionally carry further functional groups,
   and
   n represents a number $\geq 1$.

4. The process of claim 1, wherein (3) said ortho-ester of a carboxylic acid is selected from the group consisting of an ortho-ester of formic acid, an ortho-ester of acetic acid and an ortho-ester of propionic acid.

5. The process of claim 4, wherein (3) said ortho-ester is selected from the group consisting of trimethyl orthoformate, triethyl orthoformate, trimethyl orthoacetate, triethyl orthoacetate, trimethyl orthopropionate, triethyl orthopropionate and mixtures thereof.

6. The process according to claim 1, wherein (3) said ortho-ester of carbonic acid corresponds to the general structure:

$$C(OR^5)(OR^6)(OR^7)(OR^8)$$

wherein:
   $R^5$ to $R^8$: each individually represent an aliphatic, cycloaliphatic, aromatic or araliphatic hydrocarbon radical which can optionally contain heteroatoms and which can optionally contain further functional groups.

7. The process of claim 1, wherein (3) said ortho-ester is selected from the group consisting of tetramethyl orthocarbonate, tetraethyl orthocarbonate and mixtures thereof.

8. The process of claim 1, wherein (3) said ortho-ester of silicic acid corresponds to the general structure:

$$Si(OR^9)(OR^{10})(OR^{11})(OR^{12})$$

wherein:
   $R^9$ to $R^{12}$: each individually represent an aliphatic, cycloaliphatic, aromatic or araliphatic hydrocarbon radical which can optionally contain heteroatoms and which can optionally contain further functional groups.

9. The process of claim 1, wherein (3) said ortho-ester of silicic acid is selected from the group consisting of tetramethyl orthosilicate, tetraethyl orthosilicate and mixtures thereof.

10. The process of claim 1, wherein (3) said ortho-ester is added immediately before, at the same time as, or after the addition of (2) said catalyst.

11. The process of claim 1, wherein (3) said ortho-ester is present in concentrations of $\leq 1,000$ ppm, based on the total weight of the isocyanate employed.

12. The process of claim 11, wherein (3) said ortho-ester is present in concentrations of $\leq 250$ ppm, based on the total weight of the isocyanate employed.

13. The process of claim 11, wherein (3) said ortho-ester is present in concentrations of $\leq 100$ ppm, based on the total weight of the isocyanate employed.

14. The process of claim 10, wherein (3) said ortho-ester is added without dilution.

15. The process of claim 10, wherein (3) said ortho-ester is added as a masterbatch in the starting isocyanate or previously carbodiimidized isocyanate.

16. A process for the preparation of isocyanate blends comprising blending one or more of the organic isocyanates containing carbodiimide and/or uretonimine groups of claim 1, with a second isocyanate component.

17. A process for the preparation of polyisocyanate prepolymers or polyurethanes comprising reacting one or more of the organic isocyanates containing carbodiimide and/or uretonimine groups of claim 1 with one or more compounds containing isocyanate-reactive groups.

* * * * *